(12) United States Patent
Lin

(10) Patent No.: US 8,709,510 B2
(45) Date of Patent: Apr. 29, 2014

(54) COMPOSITION FOR ENHANCING MEMORY AND MITIGATING NEURODEGENERATION AND METHOD THEREOF

(71) Applicant: Sun Plaza International Co., Ltd., New Taipei (TW)

(72) Inventor: Che-Hao Lin, New Taipei (TW)

(73) Assignee: Sun Plaza International Co., Ltd., New Taipei (TW)

( * ) Notice: Subject to any disclaimer, the term of this patent is extended or adjusted under 35 U.S.C. 154(b) by 0 days.

(21) Appl. No.: 14/047,657

(22) Filed: Oct. 7, 2013

(65) Prior Publication Data

US 2014/0079817 A1    Mar. 20, 2014

Related U.S. Application Data

(63) Continuation-in-part of application No. 13/616,837, filed on Sep. 14, 2012.

(51) Int. Cl.
*A01N 65/00*    (2009.01)

(52) U.S. Cl.
USPC .......................................................... 424/725

(58) Field of Classification Search
None
See application file for complete search history.

(56) References Cited

U.S. PATENT DOCUMENTS 7,368,133 B2 *    5/2008    Wu et al. ..................... 424/725

* cited by examiner

*Primary Examiner* — Michael Meller
(74) *Attorney, Agent, or Firm* — WPAT, P.C.; Anthony King

(57) ABSTRACT

The present invention provides a composition for enhancing memory and mitigating neurodegeneration comprising an effective amount of a *Ludwigia octovalvis* extract. Also disclosed is a method thereof for enhancing memory and mitigating neurodegeneration comprising administering to a subject in need thereof an effective amount of a *Ludwigia octovalvis* extract. The composition and method of the present invention is useful in treating Alzheimer's disease.

1 Claim, 3 Drawing Sheets

COMPOSITION FOR ENHANCING MEMORY AND MITIGATING NEURODEGENERATION AND METHOD THEREOF

CROSS REFERENCE TO RELATED APPLICATIONS

This patent application is a continuation in part of U.S. patent application Ser. No. 13/616,837 filed on Sep. 14, 2012, which is hereby incorporated by reference in its entirety.

FIELD OF THE INVENTION

The present invention relates to a composition for enhancing memory and mitigating neurodegeneration and a method thereof.

BACKGROUND OF THE INVENTION

With the tendency of global population aging, many countries are facing the problem of Alzheimer's disease of their citizens. According to a research, an estimation of approximately more than 24 million people suffers from this disease all over the world. As Alzheimer's disease progresses, a patient will need care in each aspects of life, such as bathing, eating, and toileting. Since patients having Alzheimer's disease require almost 24 hour care, daily life of their family members is usually greatly impacted.

So far, there is still no accurate diagnosis or effective treatment for Alzheimer's disease, and thus the scientists are committed to the research and development of new drugs or new treatment method for treating this disease. Therefore, there is still a need for composition or method for enhancing memory and mitigating neurodegeneration, and for treating Alzheimer's disease.

SUMMARY OF THE INVENTION

This invention is based on the unexpected findings that a *Ludwigia octovalvis* extract is effective in enhancing memory and mitigating neurodegeneration, and in treating Alzheimer's disease.

Therefore, in one aspect, the present invention provides a composition for enhancing memory and mitigating neurodegeneration comprising an effective amount of a *Ludwigia octovalvis* extract.

In another aspect, the present invention provides a method for enhancing memory and mitigating neurodegeneration comprising administering to a subject in need thereof an effective amount of a *Ludwigia octovalvis* extract.

In preferred embodiments of the present invention, the *Ludwigia octovalvis* extract is a *Ludwigia octovalvis* water extract or a *Ludwigia octovalvis* alcohol extract. In one embodiment, the *Ludwigia octovalvis* extract is a *Ludwigia octovalvis* ethanol extract.

The *Ludwigia octovalvis* extract may be prepared by a method comprising the following steps: (i) extracting *Ludwigia octovalvis* with a first solution to obtain an extract solution and a residue; and (ii) removing the residue.

BRIEF DESCRIPTION OF THE DRAWINGS

The foregoing summary, as well as the following detailed description of the invention, will be better understood when read in conjunction with the appended drawing. In the drawings.

DESCRIPTION OF THE INVENTION

Figure 1:
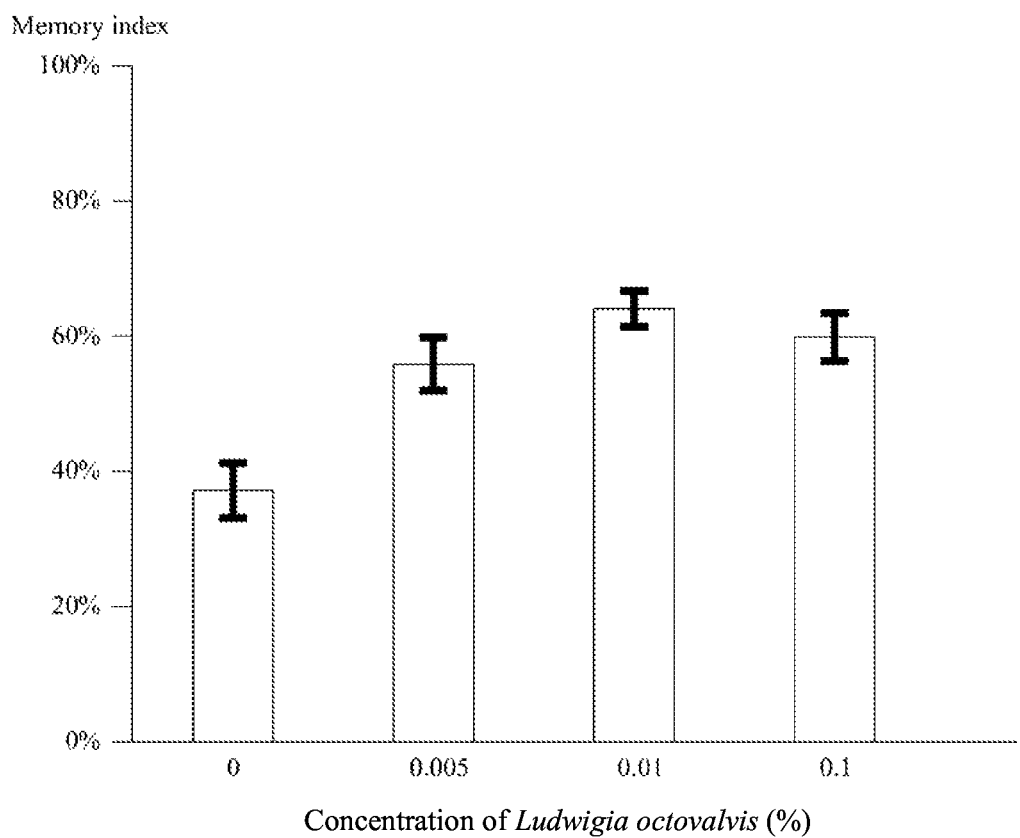
FIG. 1 shows the memory indexes of fruit flies fed on foods without the *Ludwigia octovalvis* extract, or fed on foods containing 0.005%, 0.01% or 0.1% of the *Ludwigia octovalvis* extract.

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a sample" includes a plurality of such samples and equivalents thereof known to those skilled in the art.

According to the invention, it was unexpectedly found that a *Ludwigia octovalvis* extract is effective in enhancing memory and mitigating neurodegeneration, and in treating Alzheimer's disease.

Therefore, in one aspect, the present invention provides a composition for enhancing memory and mitigating neurodegeneration comprising an effective amount of a *Ludwigia octovalvis* extract.

In one embodiment of the invention, the composition is effective in enhancing short-term memory. According to another embodiment, the composition of the present invention is useful in treating Alzheimer's disease. In another embodiment, the composition is effective in enhancing long-term memory of a subject.

According to certain embodiments of the invention, the *Ludwigia octovalvis* extract is a *Ludwigia octovalvis* water extract or a *Ludwigia octovalvis* alcohol extract. In one embodiment, the *Ludwigia octovalvis* extract is a *Ludwigia octovalvis* ethanol extract.

The *Ludwigia octovalvis* extract may be prepared by a method comprising the following steps: (i) extracting *Ludwigia octovalvis* with a first solution to obtain an extract solution and a residue; and (ii) removing the residue.

In one embodiment of the present invention, the first solution used in step (i) of the method is at a temperature of 2-10° C.

In one embodiment of the present invention, the *Ludwigia octovalvis* is extracted with the first solution for 4-12 hours in step (i) of the method. In another embodiment, the *Ludwigia octovalvis* is extracted with the first solution for 4-12 hours and then is heated for 10-60 minutes for further extraction.

According to the present invention, water or an alcohol solution may be used as the first solution in step (i) of the method. Preferably, ethanol is used as the first solution in step (i) of the method.

In another aspect, the present invention provides a method for enhancing memory and mitigating neurodegeneration comprising administering to a subject in need thereof an effective amount of a *Ludwigia octovalvis* extract.

The method of the present invention may also be used to treat Alzheimer's disease.

As used herein, the term "effective amount" or "therapeutic effective amount" refers to the amount necessary to elicit the desired biological response. In accordance with the subject invention, the effective amount is the amount of a *Ludwigia octovalvis* extract of this invention and optionally at least one additional therapeutic or active agent necessary to enhance memory or treat and/or ameliorate neurodegeneration or Alzheimer's disease.

In one embodiment of the invention, short-term memory of the subject is enhanced by the method of the present invention. According to the present invention, the method may also be used to enhance long-term memory of the subject.

According to certain embodiments of the invention, the *Ludwigia octovalvis* extract is a *Ludwigia octovalvis* water extract or a *Ludwigia octovalvis* alcohol extract. In one embodiment, the *Ludwigia octovalvis* extract is a *Ludwigia octovalvis* ethanol extract.

The *Ludwigia octovalvis* extract used in the method of the present invention may be prepared by a preparation method comprising the following steps: (i) extracting *Ludwigia octovalvis* with a first solution to obtain an extract solution and a residue; and (ii) removing the residue.

In one embodiment of the present invention, the first solution used in step (i) of the preparation method is at a temperature of 2-10° C.

In one embodiment of the present invention, the *Ludwigia octovalvis* is extracted with the first solution for 4-12 hours in step (i) of the preparation method. In another embodiment, the *Ludwigia octovalvis* is extracted with the first solution for 4-12 hours and then is heated for 10-60 minutes for further extraction.

According to the present invention, water or an alcohol solution may be used as the first solution in step (i) of the preparation method. Preferably, ethanol is used as the first solution in step (i).

To use any of the *Ludwigia octovalvis* extract described herein for enhancing memory and mitigating neurodegeneration, or treating Alzheimer's disease, the extract can be formulated as a pharmaceutical composition and administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A skilled person in the art would know how to select a buffer or carrier for administration, and the volume and the effective amount may easily be determined according to his knowledge and standard methodology of merely routine experimentation based on the present disclosure. Moreover, a skilled person in the art can mix any well known active agent with the *Ludwigia octovalvis* extract for administration to improve the therapeutic effect.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. An *Ludwigia octovalvis* extract-containing composition can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. For example, solubilizing agents such as cyclodextrins, which form specific, more soluble complexes with the *Ludwigia octovalvis* extract, or one or more solubilizing agents, can be utilized as pharmaceutical excipients for delivery of the *Ludwigia octovalvis* extract. Examples of other carriers include colloidal silicon dioxide, magnesium stearate, cellulose, sodium lauryl sulfate, and D&C Yellow #10.

The present invention is further illustrated by the following examples, which are provided for the purpose of demonstration rather than limitation.

EXAMPLES

Example 1

Preparation of the *Ludwigia octovalvis* Extract

*Ludwigia octovalvis* is used as raw material and a predetermined amount of *Ludwigia octovalvis* is ground, after which, the ground predetermined *Ludwigia octovalvis* is dipped in a first extraction solution at a low temperature ranging 2° C.-10° C. for 4-12 hours. Then the first extraction solution is heated at the temperature ranges 50° C.-100° C. for 10-60 minutes to obtain a first *Ludwigia octovalvis* extraction solution and a *Ludwigia octovalvis* residue. The first extraction solution may be a water solution or an alcohol solution. Subsequently, the *Ludwigia octovalvis* residue is separated from the first *Ludwigia octovalvis* extraction solution. The *Ludwigia octovalvis* residue (separated from the first *Ludwigia octovalvis* extraction solution) may be dipped in a second extraction solution for extraction, heated at the temperature ranging 50° C.-100° C. for 10-60 minutes and subjected to a centrifugal filter to obtain a second *Ludwigia octovalvis* extraction solution, which, in turn, may be combined with the first *Ludwigia octovalvis* extraction solution. The extraction solution may be freeze dried and reconstituted at a concentration ranging between 0.0005%-0.5%.

Example 2

The *Ludwigia octovalvis* Extract Enhances Memory

Pavlovian Olfactory Associative Learning experiments were performed to test the effects of *Ludwigia octovalvis* extract on the learning ability (short-term memory) in fruit flies. Fruit flies were maintained under an environment of 25° C. and fed with foods containing 0%, 0.005%, 0.01% and 0.1% of the *Ludwigia octovalvis* extract. The learning ability tests were performed at 20 days of age. Two different odors, 3-OCT (3-Octanol) and 4-MCH (4-Methylcyclohexanol) disliked by fruit flies were used, and the tests were conducted in a darkroom. First, the fruit flies were exposed to 3-OCT for 60 seconds, during which, an electroshock (70 volts) is applied for a 1.5/3.5 seconds On/Off alternate manner. Immediately after 45 seconds of rest, the fruit flies were exposed to 4-MCH for 60 seconds without application of electroshock (3-OCT and 4-MCH can be exchanged alternately). The fruit flies were then allowed to rest for 30 seconds. Finally, the fruit flies were allowed to enter a T-maze with 3-OCT and 4-MCH provided at two opposing arms of the T-maze for a period of two minutes. The performance index or memory index is calculated by subtracting the number of the fruit flies entering the 3-OCT arm from those entering the 4-MCH arm, and then dividing by the total number of the fruit flies. On the other hand, the odors paired with electroshock were exchanged and the tests were carried out as described above. As shown in FIG. 1, fruit flies fed on foods without the *Ludwigia octovalvis* extract have a memory index less than 40%; fruit flies fed on foods containing 0.005% of the *Ludwigia octovalvis* extract have memory index of around 60%; and fruit flies fed on foods containing 0.01% or 0.1% of the *Ludwigia octovalvis* extract have memory index of over 60%.

Example 3

Figure 2:
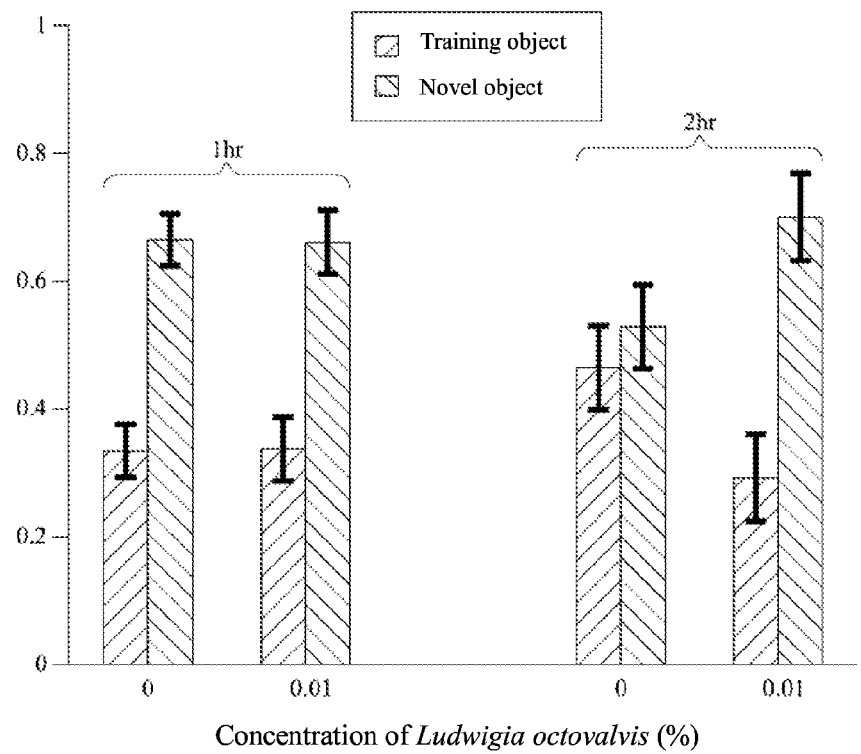
FIG. 2 shows the object recognition indexes of mice administered with different concentrations of the *Ludwigia octovalvis* extract.

The *Ludwigia octovalvis* Extract Enhances (Long-Term) Memory/Mitigating Neurodegeneration Novel object recognition task experiments were performed to evaluate the memory performance in mice. 3 months old senescence-accelerated mouse prone-8 (SAMP8) was used. It has been shown that SAMP8 has a shorter lifespan and develop Alzheimer's disease like phenotype around 6-12 months of age. In the experiments, 0 or 0.01% of the *Ludwigia octovalvis* extract were added into the drinking water of mice and the memory performances of these mice were tested after 3 months. In short, SAMP8 mice administered with 0 or 0.01% of the *Ludwigia octovalvis* extract were placed in a box (20×20×10 inches) with two different training objects placed within, to allow the mice to explore the two training objects for a training period of 5 minutes. After a period of time (1 hr or 2 hrs), one of the training objects was replaced by a new object and the mice were allowed to freely explore for another 5 minutes. The time mice spend on new object and the old object were recorded. The object recognition index is calculated by dividing the spent time for exploring the old object or a new object with the total time for exploring the old object and the new object. As shown in FIG. 2, when the memory tests were carried out one hour after the training period, the mice administered with 0% and 0.01% of the *Ludwigia octovalvis* extract both spent more time on exploring the new object than on the old object, suggesting that both groups of mice can distinguish between the trained object and the new object. However, only mice administered with 0.01% of the *Ludwigia octovalvis* extract can still distinguish the trained object and the new object when memory tests were carried out 2 hours after the training period.

Figure 3:
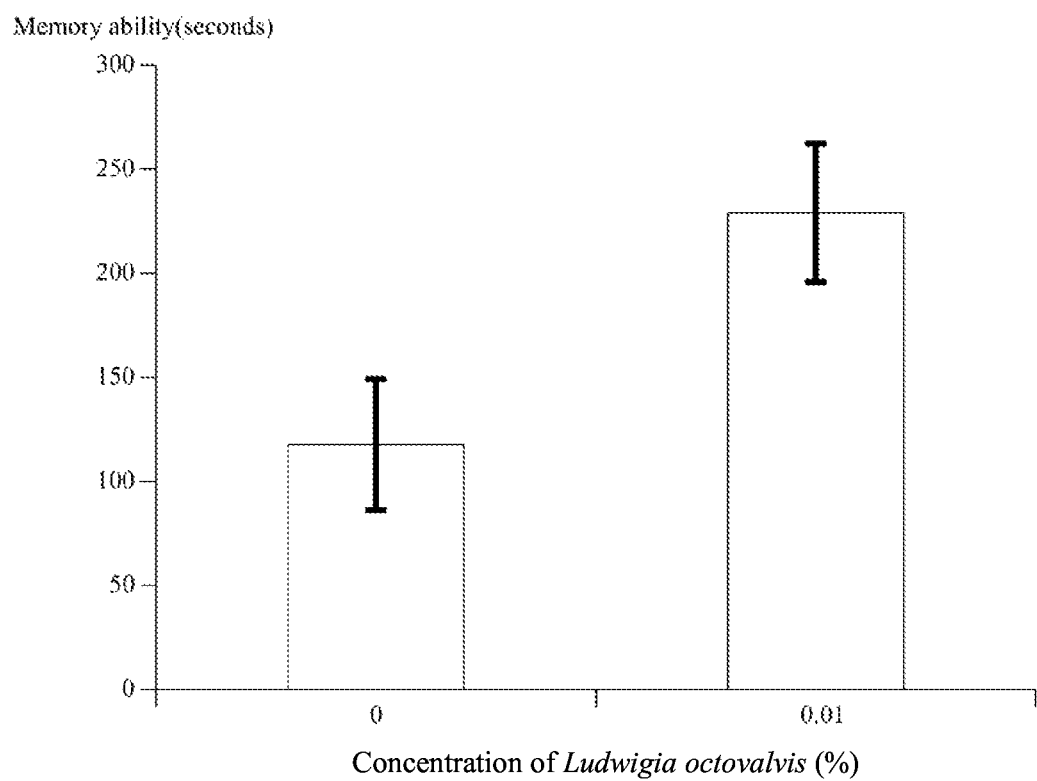
FIG. 3 shows memory ability of mice administered with different concentrations of the *Ludwigia octovalvis* extract.

Further, elevated T-maze task experiments were performed to test the memory performance in SAMP8 mice. The elevated T-maze is made of plastic and has three arms of equal dimensions (30 cm×6 cm). One arm is enclosed by walls of 16 cm high and is perpendicular to two opposing open arms. The whole apparatus was elevated 40 cm above the floor. SAMP8 mice are fed and administered with 0 and 0.01% of the *Ludwigia octovalvis* extract as described above. On the training day of the elevated T-maze task, each mouse was placed at the distal end of the enclosed arm facing the intersection of the arms and was allowed to explore the T-maze. The trial ended when the mouse entered one of the open arms by placing all four paws into the open arm or remained in the enclosed arm for a maximum time of 300 seconds. In the training session, mice were trained as many times as needed until it remains in the enclosed arm for at least 300 seconds. 24 hours after the training, mice were placed at the distal end of the enclosed arm again and the time that the animals remained in the enclosed arm was recorded and used to evaluate memory performance. As shown in FIG. 3, mice administered with 0.01% of the *Ludwigia octovalvis* extract show better memory performance on the elevated T-maze task, as they remained in the closed space for a longer period of time (an average of about 230 seconds) compared to mice without administration of the *Ludwigia octovalvis* extract (an average of about 120 seconds).

It is believed that a person of ordinary knowledge in the art where the present invention belongs can utilize the present invention to its broadest scope based on the descriptions herein with no need of further illustration. Therefore, the descriptions and claims as provided should be understood as of demonstrative purpose instead of limitative in any way to the scope of the present invention.

I claim:
1. A method for treating Alzheimer's disease in a human in need thereof comprising administering a therapeutically effective amount of an extract of *Ludwigia octovalvis* to said human to treat Alzheimer's disease in said human.

* * * * *